(12) United States Patent
Fan et al.

(10) Patent No.: US 10,464,062 B2
(45) Date of Patent: Nov. 5, 2019

(54) THREE-DIMENSIONAL MICROFLUIDIC PLATFORM AND SYSTEM AND METHOD FOR MANUFACTURING THE SAME

(71) Applicant: National Taiwan University, Taipei (TW)

(72) Inventors: Shih-Kang Fan, Taipei (TW); Min-Yu Chiang, Taipei (TW)

(73) Assignee: National Taiwan University, Taipei (TW)

( * ) Notice: Subject to any disclaimer, the term of this patent is extended or adjusted under 35 U.S.C. 154(b) by 163 days.

(21) Appl. No.: 15/795,220

(22) Filed: Oct. 26, 2017

(65) Prior Publication Data

US 2018/0297027 A1 Oct. 18, 2018

Related U.S. Application Data

(60) Provisional application No. 62/484,946, filed on Apr. 13, 2017.

(51) Int. Cl.
| | |
|---|---|
| *B01L 3/00* | (2006.01) |
| *G01N 27/447* | (2006.01) |
| *B29C 59/00* | (2006.01) |
| *B29C 67/00* | (2017.01) |

(52) U.S. Cl.
CPC ... *B01L 3/502707* (2013.01); *B01L 3/502715* (2013.01); *B29C 59/00* (2013.01); *G01N 27/44704* (2013.01); *G01N 27/44791* (2013.01); *B01L 2300/0645* (2013.01); *B01L 2300/0816* (2013.01); *B01L 2300/0874* (2013.01); *B01L 2300/0887* (2013.01); *B01L 2300/12* (2013.01)

(58) Field of Classification Search
CPC ..... B01L 2300/0645; B01L 2300/0816; B01L 2300/0874; B01L 2300/0887; B01L 2300/12; B01L 3/502707; B01L 3/502715; B29C 59/00; G01N 27/44704; G01N 27/44791
See application file for complete search history.

(56) References Cited

U.S. PATENT DOCUMENTS

| | | | | |
|---|---|---|---|---|
| 2015/0309473 | A1* | 10/2015 | Spadaccini | ........ G03H 1/2294 359/3 |
| 2016/0158748 | A1 | 6/2016 | Wu et al. | |

FOREIGN PATENT DOCUMENTS

| | | |
|---|---|---|
| CN | 102671724 | 9/2012 |
| TW | I372137 | 9/2012 |

OTHER PUBLICATIONS

Min-Yu Chiang et al., "Constructing 3D heterogeneous hydrogels from electrically manipulated prepolymer droplets and crosslinked microgels", Sci. Adv., Oct. 26, 2016, pp. 1-8.

\* cited by examiner

*Primary Examiner* — Jennifer Wecker
(74) *Attorney, Agent, or Firm* — JCIPRNET

(57) ABSTRACT

A three-dimensional microfluidic platform including a substrate and a heterogeneous structure is provided. The heterogeneous structure located on the substrate includes prepolymer pattern, cured products, or a combination of at least one prepolymer patterns and at least one cured products, where the material characteristics of the cured products are different from each other, and the material characteristics of the prepolymer patterns are different from each other.

17 Claims, 9 Drawing Sheets

THREE-DIMENSIONAL MICROFLUIDIC PLATFORM AND SYSTEM AND METHOD FOR MANUFACTURING THE SAME

CROSS-REFERENCE TO RELATED APPLICATION

This application claims the priority benefit of U.S. provisional application Ser. No. 62/484,946, filed on Apr. 13, 2017. The entirety of the above-mentioned patent application is hereby incorporated by reference herein and made a part of this specification.

BACKGROUND OF THE INVENTION

Field of the Invention

The invention relates to a microfluidic platform, and particularly relates to a three-dimensional microfluidic platform and a method for manufacturing the same.

Description of Related Art

As a microfluidic system has a plenty of advantages, such as a fast reaction speed, a high sensitivity and a low cost, etc., it is one of the most widely researched and valuable products at present. However, the microfluidic system generally has a fixed microchannel network, and after manufacturing of the microfluidic system is completed, the microchannel network thereof cannot be changed to let a fluid to flow in different directions. Moreover, the current manufacturing method of the microfluidic system does not have a characteristic of programmability, and the manufactured microfluidic system limited to a specific material or shape cannot be adapted to various application domains.

Therefore, how to make the microfluidic system not limited to the specific material or shape, and form the microfluidic system through the programmability so as to improve applicability thereof is one of the subjects currently being actively studied by related technicians of the field.

SUMMARY OF THE INVENTION

The invention is directed to a three-dimensional (3D) microfluidic platform, which has wider applicability.

The invention is directed to a method for manufacturing a 3D microfluidic platform, which has a characteristic of programmability.

The invention provides a 3D microfluidic platform including a substrate and a heterogeneous structure. The heterogeneous structure is located on the substrate, and includes prepolymer patterns, cured products, or a combination of at least one prepolymer patterns and at least one cured products, and material characteristics of the cured products are different from each other, and material characteristics of the prepolymer patterns are different from each other.

According to an embodiment of the invention, in the 3D microfluidic platform, the substrate includes an electrode layer, a dielectric layer, a hydrophobic layer or a combination thereof.

According to an embodiment of the invention, in the 3D microfluidic platform, materials of the cured products are different from each other.

According to an embodiment of the invention, the 3D microfluidic platform further includes an additive. The additive is located in at least one of the cured products or on a surface of at least one of the cured products.

According to an embodiment of the invention, in the 3D microfluidic platform, the additive includes organic particles, inorganic particles, cells or a combination thereof.

The invention provides a manufacturing system of a 3D microfluidic platform, which includes a first electrode structure, a second electrode structure and storage tanks. The second electrode structure is located above the first electrode structure, where a containing space exists between the second electrode structure and the first electrode structure for containing a heterogeneous structure. The storage tanks are located around the containing space, and the storage tanks respectively store prepolymer raw materials, where material characteristics of at least two of the prepolymer raw materials are different from each other.

According to an embodiment of the invention, the manufacturing system of the 3D microfluidic platform further includes an additive. The additive is located in at least one of the prepolymer raw materials.

According to an embodiment of the invention, in the manufacturing system of the 3D microfluidic platform, the additive includes organic particles, inorganic particles, cells or a combination thereof.

According to an embodiment of the invention, the manufacturing system of the 3D microfluidic platform further includes a first hydrophobic layer and a second hydrophobic layer. The first hydrophobic layer is located between the first electrode structure and the containing space. The second hydrophobic layer is located between the second electrode structure and the containing space.

According to an embodiment of the invention, in the manufacturing system of the 3D microfluidic platform, the first electrode structure includes a first substrate and a patterned electrode layer located on the first substrate, and the second electrode structure includes a second substrate and a continuous electrode layer located on the second substrate, where the containing space is located between the pattered electrode layer and the continuous electrode layer.

According to an embodiment of the invention, in the manufacturing system of the 3D microfluidic platform, the first electrode structure further includes a dielectric layer. The dielectric layer is located between the first hydrophobic layer and the patterned electrode layer, and the dielectric layer covers the patterned electrode layer.

The invention provides a method for manufacturing a 3D microfluidic platform, which includes following steps. A substrate is provided. A heterogeneous structure is formed on the substrate, where the heterogeneous structure includes prepolymer patterns, cured products, or a combination of at least one prepolymer pattern and at least one cured product, and material characteristics of the cured products are different from each other, and material characteristics of the prepolymer patterns are different from each other.

According to an embodiment of the invention, in the method for manufacturing the 3D microfluidic platform, the step of forming the heterogeneous structure on the substrate includes: providing prepolymer raw materials, where material characteristics of at least two of the prepolymer raw materials are different from each other; moving the prepolymer raw materials to the substrate to form prepolymer patterns on the substrate, where each of the prepolymer patterns includes one of the prepolymer raw materials or at least two of the prepolymer raw materials; and curing the prepolymer patterns to form the cured products.

According to an embodiment of the invention, the method for manufacturing the 3D microfluidic platform further comprises adding an additive to at least one of the prepolymer raw materials before moving the prepolymer raw materials to the substrate.

According to an embodiment of the invention, the method for manufacturing the 3D microfluidic platform further comprises arranging the additive after the prepolymer patterns are formed on the substrate, so as to form an additive pattern in at least one of the prepolymer patterns.

According to an embodiment of the invention, in the method for manufacturing the 3D microfluidic platform, the step of arranging the additive includes exerting an electric field to the additive.

According to an embodiment of the invention, the method for manufacturing the 3D microfluidic platform further includes forming the additive on a surface of at least one of the cured products after the cured products are formed.

According to an embodiment of the invention, in the method for manufacturing the 3D microfluidic platform, the step of moving the prepolymer raw materials to the substrate includes dielectrophoresis, electrowetting or a combination thereof.

According to an embodiment of the invention, the method for manufacturing the 3D microfluidic platform further includes moving, arranging, stacking or assembling the cured products after the cured products are formed.

According to an embodiment of the invention, in the method for manufacturing the 3D microfluidic platform, a step of moving, arranging, stacking or assembling the cured products includes dielectrophoresis, electrowetting or a combination thereof.

According to the above descriptions, in the 3D microfluidic platform and the method for manufacturing the same, the heterogeneous structure includes cured products with material characteristics different from each other, so that the 3D microfluidic platform has wider applicability. Besides, in the manufacturing system of the 3D microfluidic platform, the material characteristics of at least two of the prepolymer raw materials are different from each other, so that through a programmable control, the prepolymer raw materials are moved or arranged to predetermined positions on the substrate, or mixed at the predetermined positions of the substrate. In this way, the cured products with different material characteristics may be simply formed in the subsequent manufacturing process, and the microfluidic system is not limited to a specific material or shape.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
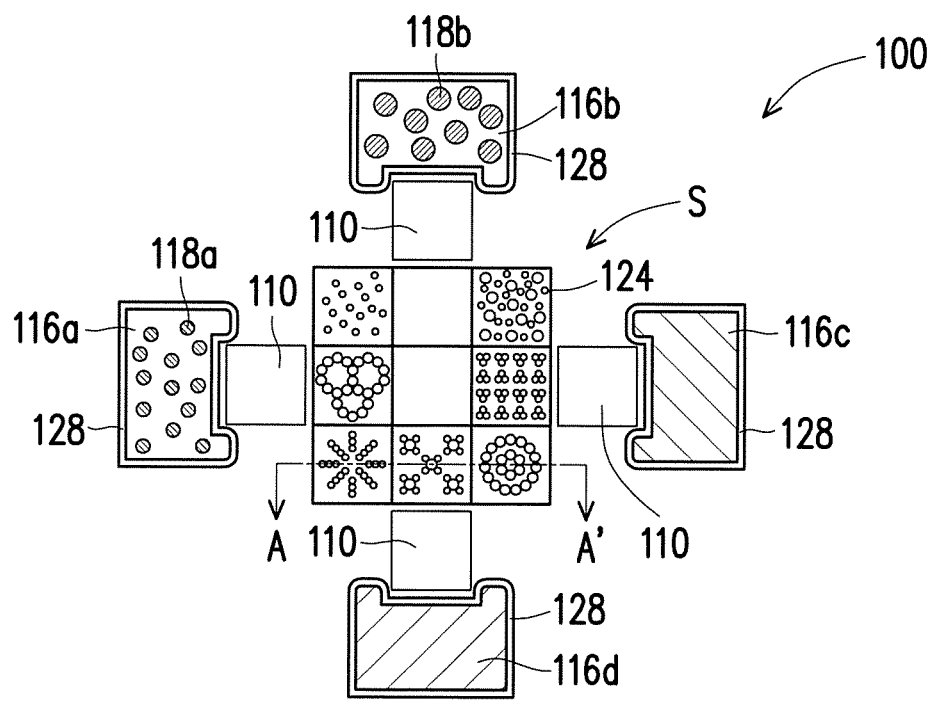
FIG. 1 is a top view of a manufacturing system of a three-dimensional (3D) microfluidic platform according to an embodiment of the invention.

The present invention will now be described more fully with reference to the accompanying drawings. However, the invention can be embodied in various forms, and is not limited to the embodiments provided below. The thickness of the layers and regions in the drawings is enlarged for clarity's sake. The same reference numbers are used in the drawings and the description to refer to the same or like parts, and descriptions of the same parts are not repeated in following paragraphs. Moreover, the terms used herein such as "above", "below", "front", "back", "left" and "right" are for the purpose of describing directions in the figures only and are not intended to be limiting of the invention.

Figure 2:
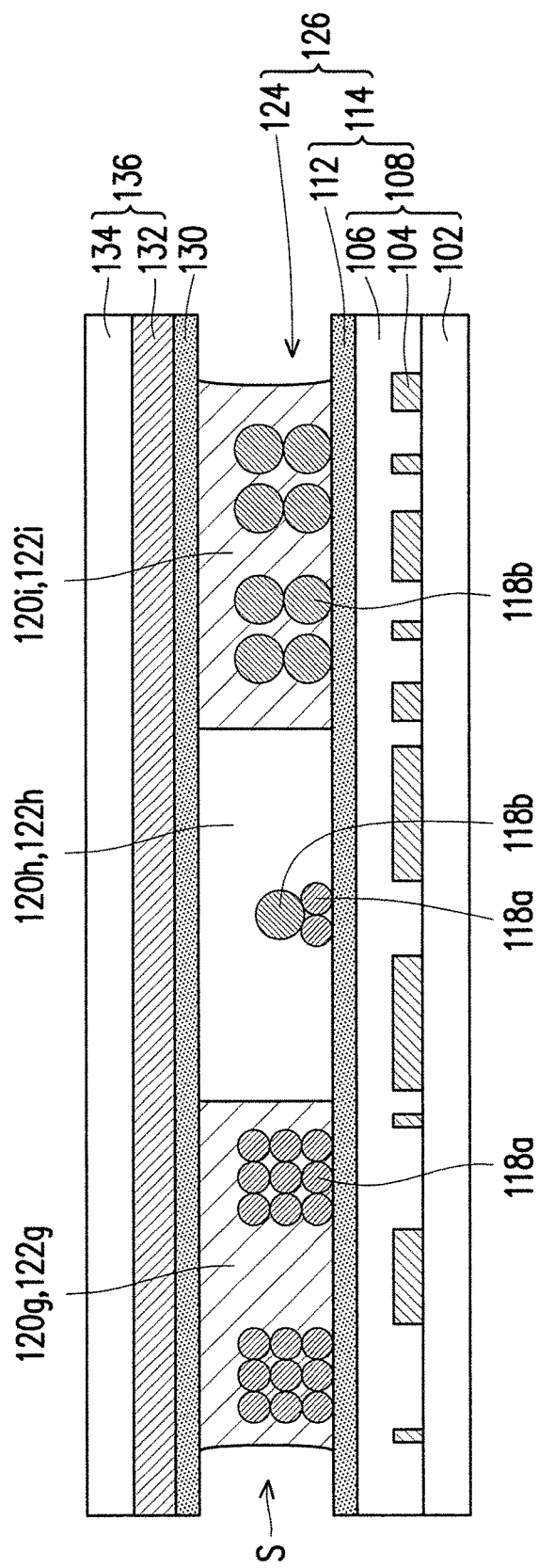
FIG. 2 is a cross-sectional view of FIG. 1 along a section line A-A'.
Figure 5:
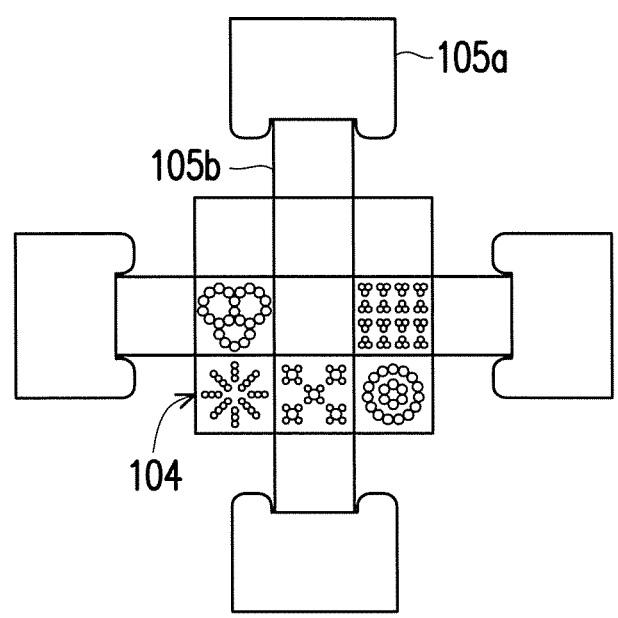
FIG. 5 is a top view of a first electrode structure of the manufacturing system of the 3D microfluidic platform according to an embodiment of the invention.

FIG. 1 is a top view of a manufacturing system of a three-dimensional (3D) microfluidic platform according to an embodiment of the invention. A second electrode structure 136 on a heterogeneous structure 124 is omitted in FIG. 1 in order to clearly present a relative position of the heterogeneous structure 124 and a containing space S used for containing the heterogeneous structure 124. FIG. 2 is a cross-sectional view of FIG. 1 along a section line A-A'. FIG. 5 is a top view of a first electrode structure of the manufacturing system of the 3D microfluidic platform according to an embodiment of the invention.

Referring to FIG. 1 and FIG. 2, the manufacturing system of the 3D microfluidic platform 100 includes a first electrode structure 108, a second electrode structure 136 and a plurality of storage tanks 128.

The first electrode structure 108 includes a first substrate 102 and a patterned electrode layer 104. The material of the first substrate 102 is, for example, glass, silicon substrate, polydimethylsiloxane (PDMS), polyethylene terephthalate (PET), polyethylene naphthalate (PEN) or a flexible polymer material, etc. In some embodiments, as shown in FIG. 5, the first electrode structure 108 further includes a storage tank electrode 105$a$ and a channel electrode 105$b$ respectively corresponding to the storage tank 128 and a channel 110.

The patterned electrode layer 104 is located on the first substrate 102. The material of the patterned electrode layer 104 may be a conductive metal material, a conductive polymer material or a conductive oxide material, etc., for example, copper, chrome, metal or indium tin oxide (ITO), etc. In some embodiments, a method for forming the patterned electrode layer 104 may be, for example, first forming an electrode material layer (not shown) on the first substrate 102 by using an E-beam evaporation method, a physical vapor deposition (PVD) method or a sputtering method, etc., and then performing a patterning process to the electrode material layer. The patterning process may be, for example, a lithographic etching process.

The second electrode structure 136 is located above the first electrode structure 108, where the containing space S exists between the second electrode structure 136 and the first electrode structure 108 for containing the heterogeneous structure 124. The second electrode structure 136 includes a second substrate 134 and a continuous electrode layer 132. A material of the second substrate 134 is, for example, glass, silicon substrate, PDMS, PET, PEN or a flexible polymer material, etc.

The continuous electrode layer 132 is located on the second substrate 134, where the containing space S is located between the patterned electrode layer 104 and the continuous electrode layer 132. A material of the continuous electrode layer 132 may be a conductive metal material, a conductive polymer material or a conductive oxide material, etc., for example, copper, chrome, metal or indium tin oxide (ITO), etc. The continuous electrode layer 132 is, for example, formed on a surface of the second substrate 134 through the E-beam evaporation method, the physical vapor deposition (PVD) method or the sputtering method.

The storage tanks 128 are located around the containing space S, and the storage tanks 128 respectively store prepolymer raw materials 116a-116d, where material characteristics of at least two of the prepolymer raw materials 116a-116d are different from each other. In the present embodiment, 4 storage tanks 128 are, for example, disposed around the containing space S, though the invention is not limited thereto. The materials of the prepolymer raw materials 116a-116d are, for example, poly(ethylene glycol) diacrylate (PEGDA) hydrogel, gelatin methaciyloyl (GelMA) hydrogel or other suitable hydrogel prepolymers.

Moreover, the fact that the material characteristics of at least two of the prepolymer raw materials 116a-116d are different from each other represents that viscosities, compositions, optical characteristics, physical properties, chemical properties or biological properties, etc. of at least two of the prepolymer raw materials 116a-116d are different from each other. For example, in some embodiments, the materials of the prepolymer raw material 116c and the prepolymer raw material 116d may be different from each other, so that the prepolymer raw materials 116c and 116d have different material characteristics.

In some other embodiments, additives 118a and 118b may be respectively added to at least one of the prepolymer raw materials 116a-116d. The additives 118a, 118b added to the prepolymer raw materials 116a-116d may be the same or different. For example, different additives 118a, 118b (for example, additives with different materials, or additives with different particle sizes) may be added to the prepolymer raw material 116a and the prepolymer raw material 116b respectively, so as to change an optical characteristic (for example, a light transmittance) of the prepolymer raw materials 116a, 116b. Therefore, even if the materials of the prepolymer raw material 116a and the prepolymer raw material 116b are the same, the two prepolymer raw materials still have different material characteristics. The additives 118a, 118b may be organic particles, inorganic particles, cells or a combination thereof. For example, the additives 118a, 118b may be functional particles, cells to be cultured or drug carriers, etc.

Moreover, referring to FIG. 2, in some embodiments, a first hydrophobic layer 112 may be selectively disposed between the first electrode structure 108 and the containing space S. A material of the first hydrophobic layer 112 is, for example, Teflon or other hydrophobic material, which is to make the prepolymer raw materials 116a-116d easier to move in the containing space S. A method for forming the first hydrophobic layer 112 is, for example, chemical vapor deposition, physical vapor deposition, spin coating or a combination thereof. In some other embodiments, a second hydrophobic layer 130 may be selectively disposed between the second electrode structure 136 and the containing space S. A material of the second hydrophobic layer 130 is, for example, Teflon or other hydrophobic material, which is to make the prepolymer raw materials 116a-116d easier to move in the containing space S. A method for forming the second hydrophobic layer 130 is, for example, chemical vapor deposition, physical vapor deposition, spin coating or a combination thereof.

Moreover, in some embodiments, the first electrode structure 108 may selectively include a dielectric layer 106 disposed between the first hydrophobic layer 112 and the patterned electrode layer 104, and the dielectric layer 106 covers the patterned electrode layer 104. A material of the dielectric layer may be parylene, a photoresist material (for example, SU8), a dielectric material such as a high dielectric constant material or a low dielectric constant material, etc. A method for forming the dielectric layer 106 is, for example, chemical vapor deposition, physical vapor deposition, spin coating or a combination thereof.

Figure 3:
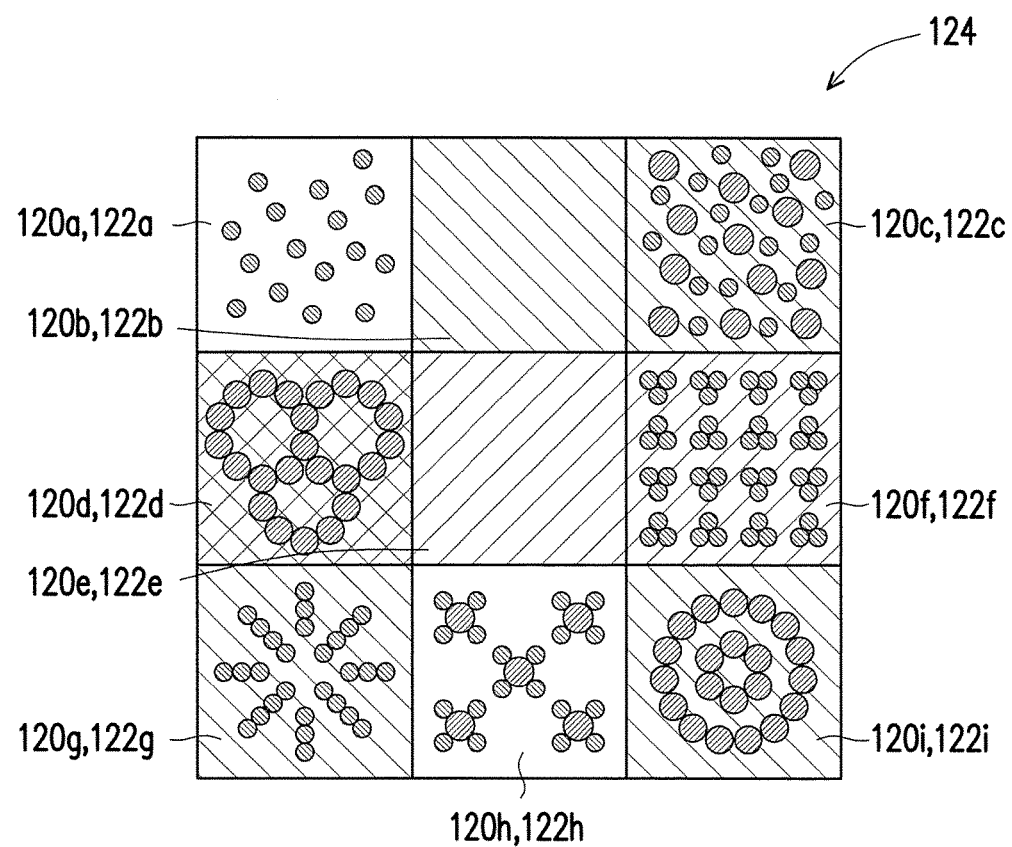
FIG. 3 is an enlarged view of a heterogeneous structure 124 in FIG. 1.
Figure 4:
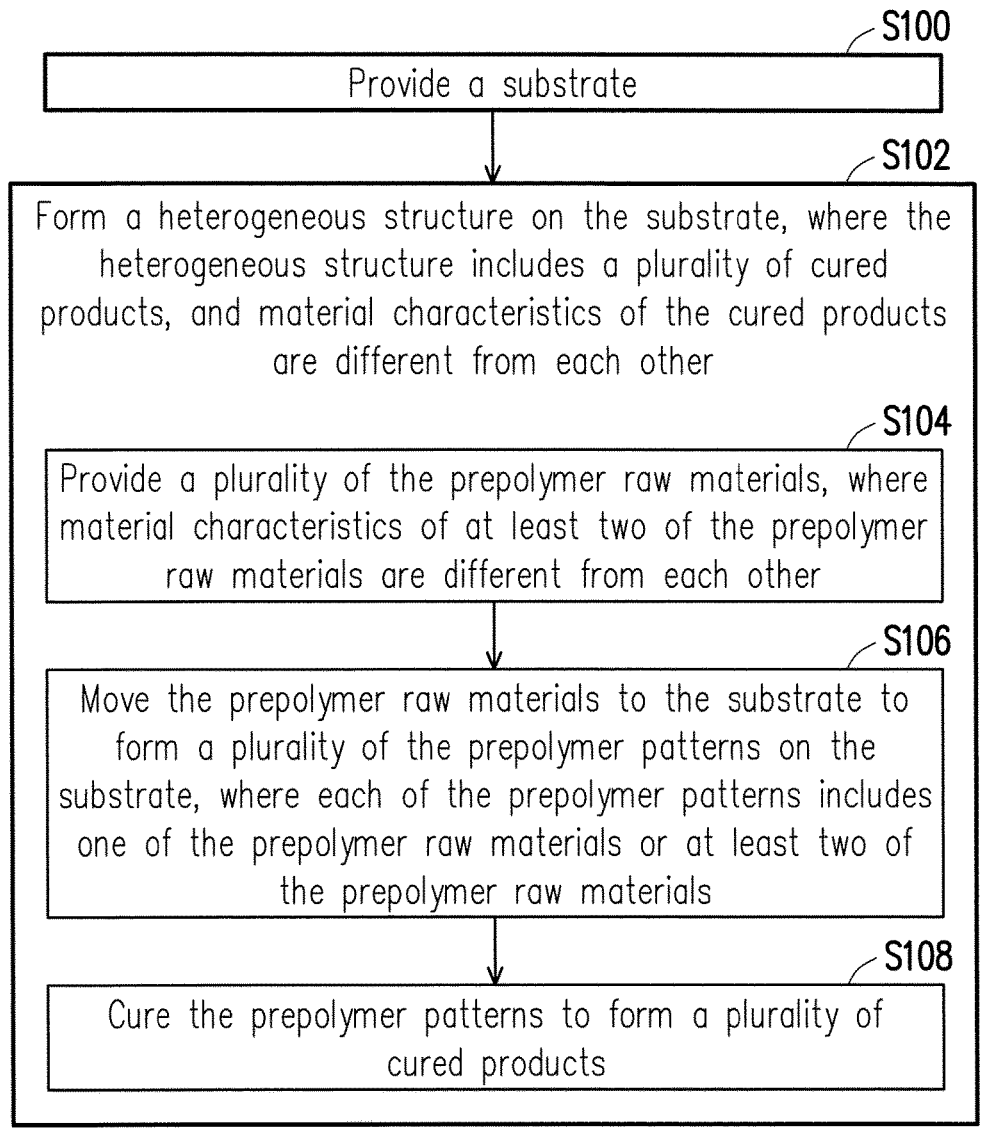
FIG. 4 is a flowchart illustrating a method for manufacturing a 3D microfluidic platform according to an embodiment of the invention.
Figure 6A:
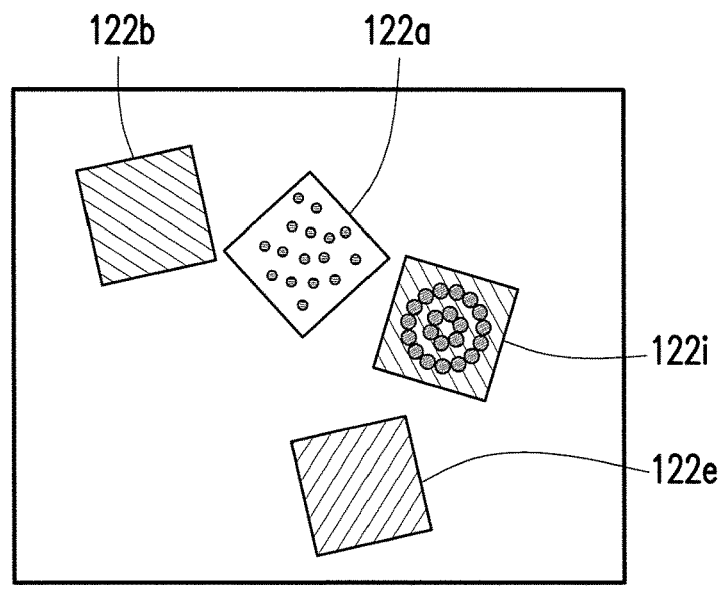
FIG. 6A to FIG. 6C are schematic diagrams of arranging cured products according to an embodiment of the invention.
Figure 6B:
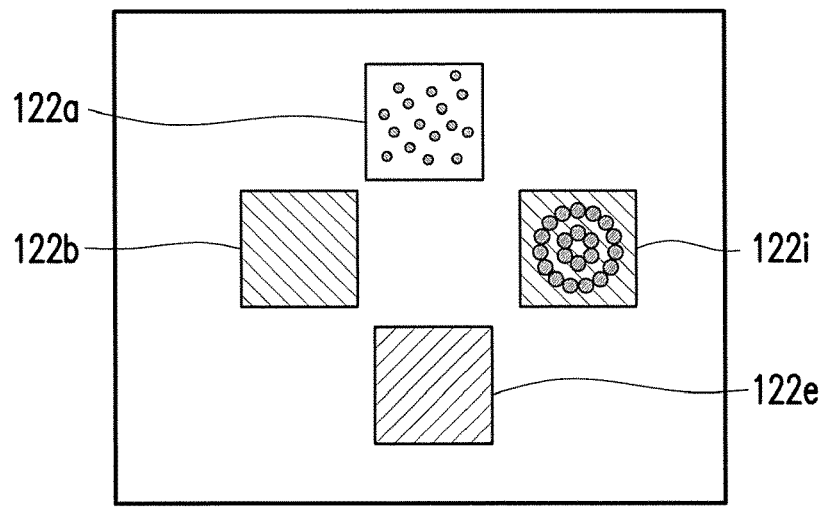
Figure 6C:
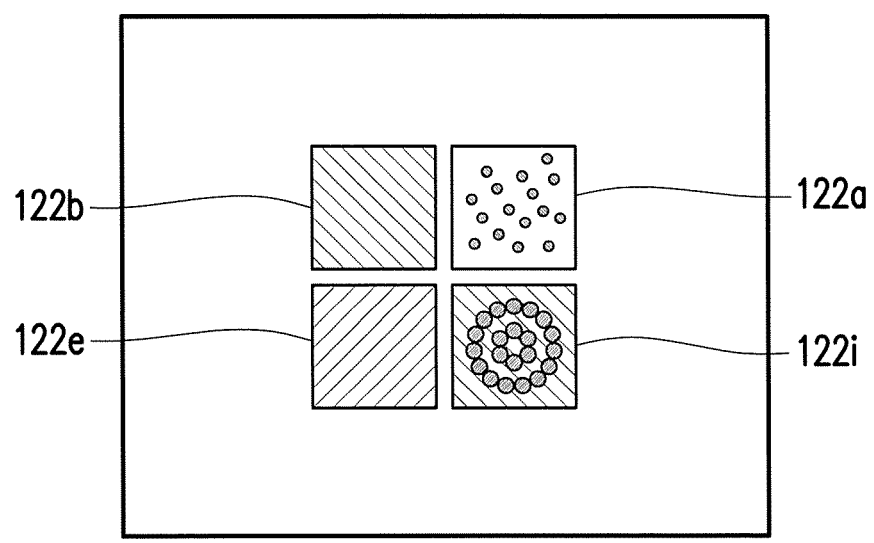
Figure 7A:
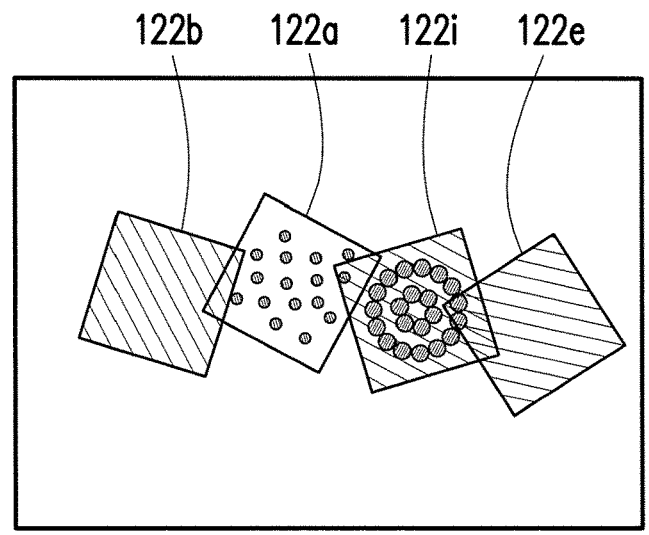
FIG. 7A to FIG. 7C are schematic diagrams of stacking cured products according to an embodiment of the invention.
Figure 7B:
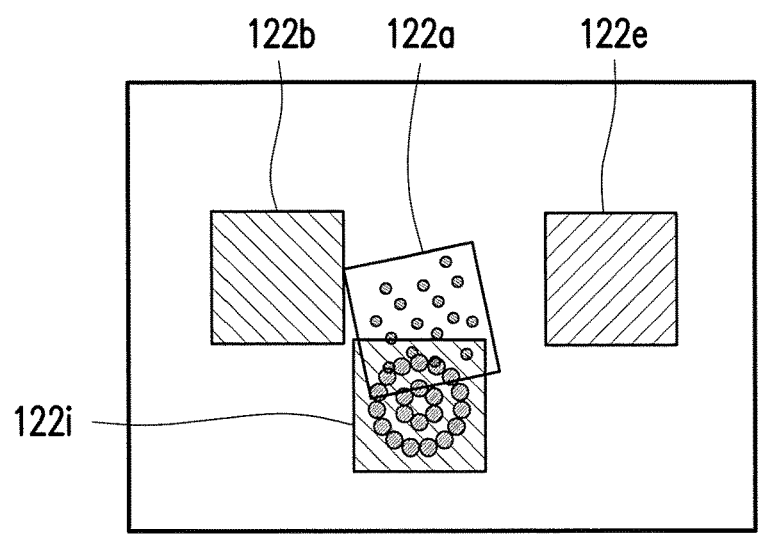
Figure 7C:
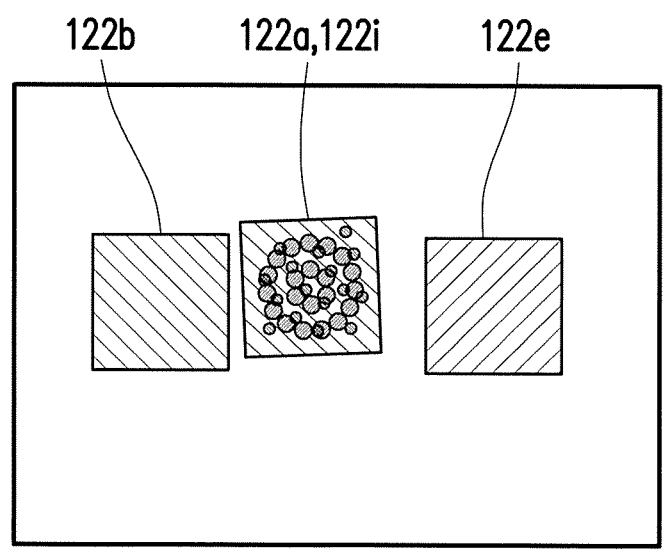

FIG. 3 is an enlarged view of the heterogeneous structure 124 in FIG. 1. FIG. 4 is a flowchart illustrating a method for manufacturing a 3D microfluidic platform according to an embodiment of the invention. FIG. 6A to FIG. 6C are schematic diagrams of arranging a plurality of cured products according to an embodiment of the invention. FIG. 7A to FIG. 7C are schematic diagrams of stacking a plurality of cured products according to an embodiment of the invention.

The method for manufacturing the 3D microfluidic platform 126 is described below with reference of FIG. 1 to FIG. 4. Moreover, although the 3D microfluidic platform 126 of the present embodiment is manufactured by the manufacturing system of the 3D microfluidic platform 100, the invention is not limited thereto.

Referring to FIG. 4, first, a step S100 is performed to provide a substrate 114. The substrate 114 may include a substrate, an electrode layer, a dielectric layer, a hydrophobic layer or a combination thereof. For example, the substrate 114 may include the first substrate 102, the patterned electrode layer 104, the dielectric layer 106 and the first hydrophobic layer 112.

Then, a step S102 is performed to form the heterogeneous structure 124 including a plurality of cured products 122a-122i, a plurality of prepolymer patterns 120a-120i or a combination thereof on the substrate 114 (as shown in FIG. 3), where material characteristics of the cured products 122a-122i are different from each other, and material characteristics of the prepolymer patterns 120a-120i are different from each other. In some embodiments, a method for forming the heterogeneous structure 124 on the substrate 114 includes following steps.

First, a step S104 is performed to provide a plurality of the prepolymer raw materials 116a-116d, and material characteristics of at least two of the prepolymer raw materials 116a-116d are different from each other. In some embodiments, the prepolymer raw materials 116a-116d may be stored in the storage tanks 128 (as shown in FIG. 1).

Then, a step S106 is performed to move the prepolymer raw materials 116a-116d to the substrate 114 so as to form a plurality of the prepolymer patterns 120a-120i on the substrate 114 (as shown in FIG. 3), where each of the prepolymer patterns 120a-120i includes one of the prepolymer raw materials 116a-116d or at least two of the prepolymer raw materials 116a-116d. The material characteristics of at least two of the prepolymer raw materials 116a-116d may be different from each other. In the present embodiment, 9 prepolymer patterns 120a-120i with different material characteristics are formed on the substrate 114, and are arranged to form a nine-block-box, though the invention is not limited thereto. Each of the prepolymer patterns 120a-120i includes one of the prepolymer raw materials 116a-116d or at least two of the prepolymer raw materials 116a-116d. For example, as shown in FIG. 3, the prepolymer pattern 120b includes a single prepolymer raw material 116c, and the prepolymer pattern 120d includes the prepolymer raw materials 116b, the prepolymer raw materials 116c and the prepolymer raw materials 116d. Namely, through programmable control, the plurality of prepolymer raw materials 116a-116d are moved to or arranged to predetermined positions on the substrate 114, so as to form the prepolymer patterns 120a-120i with different material characteristics on the substrate 114. The aforementioned programmable control represents that the prepolymer raw materials 116a-116d may be moved, arranged, assembled or mixed on the substrate 114 according to a design. In some embodiments, the prepolymer raw materials 116a-116d may be moved to the substrate 114 or arranged on the substrate 114 through dielectrophoresis or electrowetting. For example, as shown in FIG. 5, the prepolymer raw materials 116a-116d may be moved to the containing space S from the storage tanks 128 through dielectrophoresis, electrowetting or a combination thereof by using the patterned electrode layer 104, the storage tank electrode 105a and the channel electrode 105b in the first electrode structure 108. In some embodiments, the patterns of the patterned electrode layer 104 may correspond to the patterns of the prepolymer patterns 120a-120i.

Then, a step S108 is performed to cure the prepolymer patterns 120a-120i so as to form a plurality of cured products 122a-122i, where the material characteristics of the cured products 122a-122i are different from each other. In some embodiment, a portion of the prepolymer patterns may be selectively cured, so as to form a combination of at least one prepolymer patterns and at least one cured products. Moreover, in some embodiment, users may remove the non-cured prepolymer patterns according to a design, so that the cured products may be formed as predetermined pattern. Namely, the heterogeneous structure 124 in the 3D microfluidic manufacturing platform 126 includes the cured products 122a-122i with different material characteristics, and the cured products 122a-122i may be formed on the substrate 114 through programmable control. Therefore, the 3D microfluidic platform 126 with wider applicability may be formed through a simple manufacturing method, and the manufactured 3D microfluidic platform 126 is applicable for various domains such as cell culture, biological scaffold, biosensor, etc. A material of the cured products 122a-122i is, for example, PEGDA hydrogel, GelMA hydrogel or other suitable hydrogels. In some embodiments, a solution containing a PEGDA prepolymer and photo initiator may be irradiated by ultraviolet light (light intensity 100 mW/cm$^2$, light irradiation time 5 seconds) to form the PEGDA hydrogel. Moreover, in some embodiments, a solution containing a GelMA prepolymer and photo initiator may be irradiated by ultraviolet light (light intensity 70 mW/cm$^2$, light irradiation time 8 seconds) to form the GelMA hydrogel. In some embodiments, the prepolymer patterns 120a-120i may be cured through photo crosslinking, thermal crosslinking, chemical crosslinking or a combination thereof.

Moreover, referring to FIG. 1, in some embodiments, in order to form the additives 118a, 118b in the cured products 122a-122i, the additives 118a, 118b may be added to at least one of the prepolymer raw materials 116a-116d before the prepolymer raw materials 116a-116d are moved to the substrate 114. The additives 118a, 118b in the prepolymer raw materials 116a-116d may be the same or different. For example, the additives 118a, 118b may be respectively added to the prepolymer raw materials 116a, 116b. In this way, when the prepolymer raw materials 116a-116d are moved to the substrate 114 to form the prepolymer patterns 120a-120i, the additives 118a, 118b may be distributed in the prepolymer patterns 120a-120i (for example, the prepolymer patterns 120a, 120c-120d, 120f-120i shown in FIG. 3) according to a product design requirement, and then through the subsequent process of curing the prepolymer patterns, the additives 118a, 118b are formed in the cured products 122a-122i or on a surface thereof. In some other embodiments, after the cured products 122a-122i are formed, the additives 118a, 118b may be selectively formed on the surface of at least one of the cured products 122a-122i. In this way, the additives 118a, 118b may be formed in the cured products 122a-122i in a 3D distribution manner or formed on the surface of the cured products 122a-122i in a 2D distribution manner, such that a total contact surface area of the additives 118a, 118b and the cured products 122a-122i is increased, and applicability or performance of the 3D microfluidic platform 126 is enhanced. For example, when the additives 118a, 118b are cells to be cultured, the cells may grow in the cured products 122a-122i (3D distribution) and grow on the surface thereof (2D distribution), so as to increase the number of the cultured cells. Namely, the cured products 122a-122i may provide more surface area and space for growing the cells.

Besides, after the prepolymer patterns 120a-120i are formed on the substrate 114, the additives 118a, 118b located therein may be arranged, so as to form additive patterns (for example, arranging patterns of the prepolymer patterns 120a, 120c-120d, 120f-120i shown in FIG. 3) in at least one of the prepolymer patterns 120a-120i. In some embodiments, a method for arranging the additives 118a, 118b includes exerting an electric field to the additives 118a, 118b, though the invention is not limited thereto.

Moreover, in some embodiments, after the cured products 122a-122i are formed, the cured products 122a-122i may be moved, arranged, stacked or assembled to form predetermined patterns. Namely, the liquid-state prepolymer patterns 120a-120i may be moved or arranged before curing, or the solid-state cured products 122a-122i may be moved or arranged after the curing. In some embodiments, a method for moving, arranging, stacking or assembling the cured products 122a-122i may be dielectrophoresis, electrowetting or a combination thereof. For example, referring to FIG. 6A to FIG. 6C, the predetermined pattern may be achieved by moving the cured products 122a, 122b, 122e, 122i shown in FIG. 6A through dielectrophoresis, electrowetting or a combination thereof, so that the cured products may be arranged to form a pattern shown in FIG. 6B, or further arranged to form a pattern shown in FIG. 6C. Besides, referring to FIG. 7A to FIG. 7C, the predetermined pattern may also be achieved by moving the cured products 122a, 122b, 122e, 122i through dielectrophoresis, electrowetting or a combination thereof, so that the cured products may be stacked to form a pattern shown in FIG. 7A, or stacked to form a pattern shown in FIG. 7B, or further stacked form a pattern shown in FIG. 7C. Moreover, in order to decrease a friction of the cured products 122a-122i in the process of moving, arranging, stacking or assembling, in some embodiments, the cured products 122a-122i may be moved, arranged, stacked or assembled in a liquid, so as to form the predetermined pattern. The aforementioned liquid may be a prepolymer solution that is not reacted with the cured products 122a-122i, and the prepolymer solution may be cured after the predetermined pattern is formed.

Hereinafter, the 3D microfluidic platform 126 of the present embodiment is described below with reference of FIG. 2 and FIG. 3. Moreover, although the method for manufacturing the 3D microfluidic platform 126 of the present embodiment has been described above, the invention is not limited thereto.

Referring to FIG. 2 and FIG. 3, the 3D microfluidic platform 126 includes the substrate 114 and the heterogeneous structure 124, and may further include the additives 118a, 118b. The substrate 114 may include a substrate, an electrode layer, a dielectric layer, a hydrophobic layer or a combination thereof. For example, the substrate 114 may include the first substrate 102, the patterned electrode 104, the dielectric layer 106 and the first hydrophobic layer 112. The heterogeneous structure 124 is located on the substrate 114, where the heterogeneous structure 124 includes a plurality of the prepolymer patterns 120a-120i, a plurality of the cured products 122a-122i or a combination thereof. The heterogeneous structure 124 may include combinations of a plurality of the cured products 122a-122i and a plurality of the prepolymer patterns 120a-120i, or may include a combination of one of the cured products 122a-122i and one of the prepolymer patterns 120a-120i. In the present embodiment, the heterogeneous structure 124 includes a plurality of the cured products 122a-122i (i.e. the cured prepolymer patterns 120a-120i), though the invention is not limited thereto. In some other embodiments, the heterogeneous structure 124 may include a plurality of the prepolymer patterns 120a-120i, such that according to an actual design, a user may partially cure the aforementioned prepolymer patterns, and remove the non-cured prepolymer patterns, so as to pattern the heterogeneous structure 124. Moreover, in other embodiments, the non-cured prepolymer patterns 120a-120i may be retained, such that the heterogeneous structure 124 includes both of the cured products and the prepolymer patterns at the same time. The material characteristics of the cured products 122a-122i are different from each other, and the material characteristics of the prepolymer patterns 120a-120i are different from each other. In some embodiments, the materials of the cured products 122a-122i may be different from each other. In some embodiments, the materials of prepolymer patterns 120a-120i and the cured products 122a-122i are different from each other. The additives 118a, 118b are located in or on a surface of at least one of the cured products 122a-122i, and the additives 118a, 118b are, for example, organic particles, inorganic particles, cells or a combination thereof.

In summary, in the 3D microfluidic platform and the method for manufacturing the same, the heterogeneous structure includes a plurality of cured products with material characteristics different from each other, so that the 3D microfluidic platform has wider applicability. Besides, in the manufacturing system of the 3D microfluidic platform, the material characteristics of at least two of the prepolymer raw materials are different from each other, so that through the programmable control, the prepolymer raw materials are moved or arranged to predetermined positions on the substrate, or mixed at the predetermined positions of the substrate. In this way, the cured products with different material characteristics may be simply formed in the subsequent manufacturing process, and the microfluidic system is not limited to a specific material or shape.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A three-dimensional microfluidic platform, comprising:
a substrate;
a heterogeneous structure, located on the substrate, and comprising prepolymer patterns, cured products, or a combination of at least one prepolymer patterns and at least one cured products, wherein material characteristics of the cured products are different from each other, and material characteristics of the prepolymer patterns are different from each other; and
an additive, located in at least one of the cured products or on a surface of at least one of the cured products.

2. The three-dimensional microfluidic platform as claimed in claim 1, wherein the substrate comprises an electrode layer, a dielectric layer, a hydrophobic layer or a combination thereof.

3. The three-dimensional microfluidic platform as claimed in claim 1, wherein materials of the cured products are different from each other.

4. The three-dimensional microfluidic platform as claimed in claim 1, wherein the additive comprises organic particles, inorganic particles, cells or a combination thereof.

5. A manufacturing system of a three-dimensional microfluidic platform, comprising:
a first electrode structure;
a second electrode structure, located above the first electrode structure, wherein a containing space exists between the second electrode structure and the first electrode structure for containing a heterogeneous structure; and
storage tanks, located around the containing space, and the storage tanks respectively storing at least two or more prepolymer raw materials, wherein material characteristics of at least two of the prepolymer raw materials are different from each other.

6. The manufacturing system of the three-dimensional microfluidic platform as claimed in claim 5, further comprising:
an additive, located in at least one of the prepolymer raw materials.

7. The manufacturing system of the three-dimensional microfluidic platform as claimed in claim 6, wherein the additive comprises organic particles, inorganic particles, cells or a combination thereof.

8. The manufacturing system of the three-dimensional microfluidic platform as claimed in claim 5, further comprising:
a first hydrophobic layer, located between the first electrode structure and the containing space; and
a second hydrophobic layer, located between the second electrode structure and the containing space.

9. The manufacturing system of the three-dimensional microfluidic platform as claimed in claim 8, wherein
the first electrode structure comprises:
a first substrate; and
a patterned electrode layer, located on the first substrate, and
the second electrode structure comprises:
a second substrate; and
a continuous electrode layer, located on the second substrate, wherein the containing space is located between the pattered electrode layer and the continuous electrode layer.

10. The manufacturing system of the three-dimensional microfluidic platform as claimed in claim 9, wherein the first electrode structure further comprises:
a dielectric layer, located between the first hydrophobic layer and the patterned electrode layer, and the dielectric layer covers the patterned electrode layer.

11. A method for manufacturing a three-dimensional microfluidic platform, comprising:
providing a substrate;
forming a heterogeneous structure on the substrate, wherein the heterogeneous structure comprises prepolymer patterns, cured products or a combination of at least one prepolymer patterns and at least one cured products, and material characteristics of the cured products are different from each other, and material characteristics of the prepolymer patterns are different from each other;
providing prepolymer raw materials, wherein material characteristics of at least of the prepolymer raw materials are different from each other;
moving the prepolymer raw materials to the substrate to form prepolymer patterns on the substrate, wherein each of the prepolymer patterns comprises one of the prepolymer raw materials or at least two of the prepolymer raw materials;
curing the prepolymer patterns to form the cured products; and
adding an additive to at least one of the prepolymer raw materials before moving the prepolymer raw materials to the substrate.

12. The method for manufacturing the three-dimensional microfluidic platform as claimed in claim 11, further comprising: arranging the additive after the prepolymer patterns are formed on the substrate, so as to form an additive pattern in at least one of the prepolymer patterns.

13. The method for manufacturing the three-dimensional microfluidic platform as claimed in claim 12, wherein the step of arranging the additive comprises exerting an electric field to the additive.

14. The method for manufacturing the three-dimensional microfluidic platform as claimed in claim 11, further comprising: forming the additive on a surface of at least one of the cured products after the cured products are formed.

15. The method for manufacturing the three-dimensional microfluidic platform as claimed in claim 11, wherein the step of moving the prepolymer raw materials to the substrate comprises dielectrophoresis, electrowetting or a combination thereof.

16. The method for manufacturing the three-dimensional microfluidic platform as claimed in claim 11, further comprising: moving, arranging, stacking or assembling the cured products after the cured products are formed.

17. The method for manufacturing the three-dimensional microfluidic platform as claimed in claim 16, the step of moving, arranging, stacking or assembling the cured products comprises dielectrophoresis, electrowetting or a combination thereof.

* * * * *